(12) United States Patent
Obidullah et al.

(10) Patent No.: US 11,691,955 B2
(45) Date of Patent: Jul. 4, 2023

(54) PROCESS FOR RECOVERING PROPYLENE OXIDE AND CARBON DIOXIDE IN PPC POLYOL PRODUCTION

(71) Applicant: Saudi Arabian Oil Company, Dhahran (SA)

(72) Inventors: ASM Obidullah, Dhahran (SA); Omar Mohammed O AlAmoudi, Al Khubar (SA)

(73) Assignee: Saudi Arabian Oil Company, Dhahran (SA)

( * ) Notice: Subject to any disclaimer, the term of this patent is extended or adjusted under 35 U.S.C. 154(b) by 128 days.

(21) Appl. No.: 17/460,462

(22) Filed: Aug. 30, 2021

(65) Prior Publication Data

US 2023/0064622 A1 Mar. 2, 2023

(51) Int. Cl.
*C07D 301/32* (2006.01)

(52) U.S. Cl.
CPC ................... *C07D 301/32* (2013.01)

(58) Field of Classification Search
CPC ................................................. C07D 301/32
See application file for complete search history.

(56) References Cited

U.S. PATENT DOCUMENTS

| | | | |
|---|---|---|---|
| 3,287,234 A | 11/1966 | Steel et al. | |
| 3,350,418 A | 10/1967 | Bowe et al. | |
| 3,580,819 A | 5/1971 | Hoory et al. | |
| 3,632,482 A | 1/1972 | Horry et al. | |
| 3,715,284 A | 2/1973 | Burns et al. | |
| 3,881,996 A | 5/1975 | Schmidt | |
| 4,140,588 A | 2/1979 | Schmidt | |
| 7,323,579 B2 | 1/2008 | Gobbel et al. | |
| 7,594,979 B2 | 9/2009 | Patrascu et al. | |
| 7,718,040 B2 | 5/2010 | Chang | |
| 10,138,328 B2 * | 11/2018 | Müller | C08G 65/2603 |
| 2004/0133018 A1 | 7/2004 | Oku et al. | |
| 2010/0094031 A1 | 4/2010 | Trent et al. | |

FOREIGN PATENT DOCUMENTS

| | | |
|---|---|---|
| EP | 3556791 A1 | 10/2019 |
| WO | 2021005470 A1 | 1/2021 |

OTHER PUBLICATIONS

Notification of Transmittal of the International Search Report and the Written Opinion of the International Searching Authority, or the Declaration dated Nov. 3, 2022 pertaining to International application No. PCT/US2022/040087 filed Aug. 11, 2022.

Von Der Assen Niklas et al: "Life cycle assessment of polyols for polyurethane production using CO2 as feedstock: insights from an industrial case study", Green Chemistry, vol. 16, No. 6, Jan. 1, 2014, pp. 3272-3280.

* cited by examiner

*Primary Examiner* — Golam M Shameem

(74) *Attorney, Agent, or Firm* — Dinsmore & Shohl LLP

(57) ABSTRACT

In accordance with one or more embodiments of the present disclosure, a process includes introducing a mixture comprising polypropylene carbonate (PPC) polyol, carbon dioxide, propylene oxide, and at least one dibasic ester to a quenching vessel to separate the PPC polyol from the carbon dioxide and the propylene oxide; introducing additional dibasic ester to the separation vessel, thereby separating the carbon dioxide from the propylene oxide and the dibasic ester such that a mixture of propylene oxide and the dibasic ester is formed; and introducing the mixture of propylene oxide and the dibasic ester to a recovery vessel, wherein the propylene oxide is separated from the dibasic ester in the recovery vessel.

12 Claims, 1 Drawing Sheet

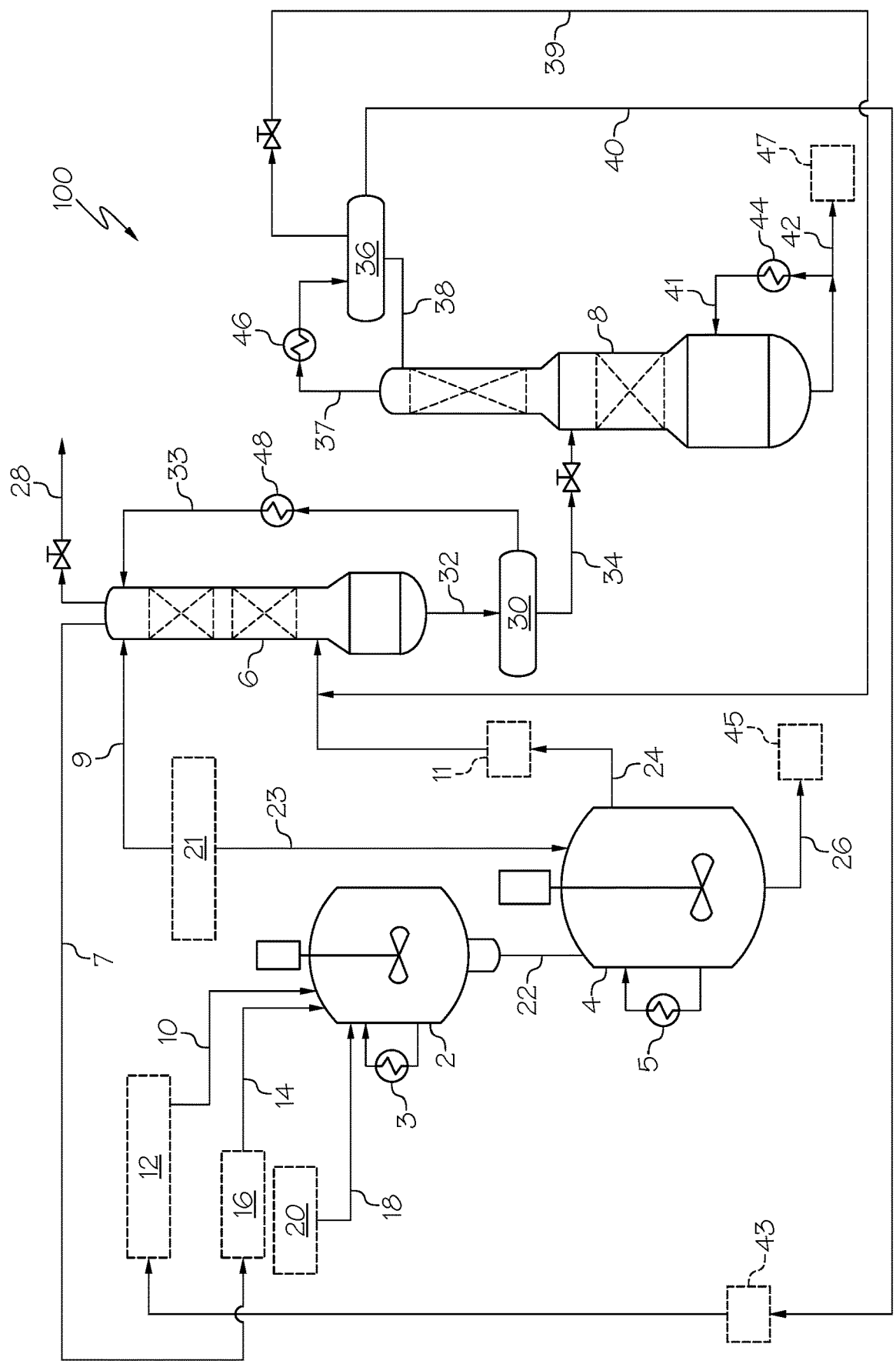

PROCESS FOR RECOVERING PROPYLENE OXIDE AND CARBON DIOXIDE IN PPC POLYOL PRODUCTION

TECHNICAL FIELD

Embodiments of the present disclosure generally relate to the production of polypropylene carbonate polyols, and pertain particularly to a process for recovering propylene oxide and carbon dioxide during the production of polypropylene carbonate polyols.

BACKGROUND

Emission of green-house gases, such as carbon dioxide ($CO_2$), is currently a major environmental concern. However, it is possible to use $CO_2$ gas as a valuable raw material for the production of certain materials, including polypropylene carbonate (PPC) polyol to be used as a prepolymer for polyurethane formation. To form PPC polyol, $CO_2$ is reacted with propylene oxide (PO) in the presence of a starter and the catalyst.

SUMMARY

After the reaction described above, unreacted $CO_2$ and PO should be separated from the reaction mixture in the downstream process. There is, therefore, a continual need for novel processes for recovering $CO_2$, PO, and solvent. Embodiments of the present disclosure are directed to a process for recovering $CO_2$ and PO from a dibasic ester solution. In embodiments, the process is based on binary vapor-liquid equilibrium (VLE) phase behavior analyses of PO—$CO_2$, dibasic ester-$CO_2$, dibasic ester-PO, and polyol-dibasic ester. In embodiments, the process is based on related thermodynamic properties and transport properties.

According to one embodiment, a process includes introducing a mixture comprising polypropylene carbonate (PPC) polyol, carbon dioxide, propylene oxide, and at least one dibasic ester to a quenching vessel to separate the PPC polyol from the carbon dioxide and the propylene oxide; introducing additional dibasic ester to the separation vessel, thereby separating the carbon dioxide from the propylene oxide and the dibasic ester such that a mixture of propylene oxide and the dibasic ester is formed; and introducing the mixture of propylene oxide and the dibasic ester to a recovery vessel, wherein the propylene oxide is separated from the dibasic ester in the recovery vessel.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which:

The FIGURE is a process flow diagram in accordance with embodiments described herein.

DETAILED DESCRIPTION

In the description and claims that follow, certain pressures within various vessels are reported with units "kPaG." The unit kPaG refers to a pressure in kPa above the ambient pressure (when the value is positive) or below the ambient pressure (when the value is negative). The term "ambient pressure" refers to the pressure outside the vessel. In most instances, and unless otherwise indicated, ambient pressure will be 100 kPa at 20° C.

As used herein, the term "conduit" includes casings, liners, pipes, tubes, coiled tubing, and mechanical structures with interior voids.

As used herein, the term "dibasic ester" refers to an ester of a dicarboxylic acid. Exemplary dibasic esters include, but are not limited to, esters of adipic acid, esters of glutaric acid, and esters of succinic acid. For example, the dibasic ester may be di-methyl adipate, di-methyl glutarate, di-methyl succinate, di-ethyl adipate, diethyl glutarate, di-ethyl succinate, or mixtures of two or more of these.

In one or more embodiments, a process for isolating PO for reuse in formation of PPC polyol may include introducing a mixture comprising $CO_2$, PO, and at least one dibasic ester to a separation vessel. In embodiments, an amount of the dibasic ester may be carried over during vacuum stripping. In such embodiments, additional fresh dibasic ester may optionally be added to the separation vessel as needed, whereupon the $CO_2$ may separate from the PO and the dibasic ester such that a mixture of PO and the dibasic ester may be formed. The mixture of PO and the dibasic ester may be introduced to a recovery vessel in which the PO may be separated from the dibasic ester. This PO may then be recycled in the process for making PPC polyol. In embodiments, the purity of the recovered PO may be at least 90%, at least 91%, at least 92%, at least 93%, at least 94%, at least 95%, at least 96%, at least 97%, at least 98%, at least 99%, or even at least 99.7%. In embodiments, the purity of the recovered dibasic ester may be at least 90%, at least 91%, at least 92%, at least 93%, at least 94%, at least 95%, at least 96%, at least 97%, at least 98%, or even at least 99%.

Referring now to the FIGURE, which shows an exemplary process flow diagram of embodiments described herein, the process for isolating PO and $CO_2$ may be appended to a process for forming PPC polyol. For instance, PPC polyol may be made by introducing $CO_2$, PO, a starter, and at least one catalyst system to a polymerization reactor 2, thereby forming a mixture comprising the PPC polyol, unreacted PO, and $CO_2$. The heat of reaction may be removed using chiller 3, thereby maintaining the desired temperature. The product from polymerization reactor 2 may be passed to quenching vessel 4, which may be equipped with heater 5 and vacuum system 11 for maintaining appropriate temperature and pressure during venting and vacuum stripping. In embodiments, the quenching vessel 4 contains a small quantity of strong acid in a dibasic ester solution. This solution quenches the polymerization reaction and reduces the viscosity of the reaction mixture for further processing. Quenching vessel 4 receives the reactor batch in a controlled manner, allowing the pressure to decrease to near atmospheric while maintaining a temperature from 30° C. to 60° C., such as from 40° C. to 50° C. or from 40° C. to 45° C. In embodiments, the pressure during the transfer may be from 20 kPa to 40 kPa, such as from 25 kPa to 35 kPa or about 30 kPa.

After completing the transfer of the reaction mixture from the polymerization reactor 2 to the quenching vessel 4, the temperature within the quenching vessel 4 may be increased and a vacuum may be applied. The increased temperature may be from 60° C. to 90° C., such as from 65° C. to 85° C. or from 70° C. to 80° C. The pressure may be reduced via the vacuum to be from 0.5 kPa to 3.5 kPa, such as from 1 kPa to 3 kPa or 1.3 kPa to 2.7 kPa. Total time for the transfer may be from 3 hours to 10 hours, such as from 3.5 hours to 10 hours, from 4 hours to 10 hours, from 4.5 hours to 10 hours, from 5 hours to 10 hours, from 5.5 hours to 10 hours, from 6 hours to 10 hours, from 6.5 hours to 10 hours, from 7 hours to 10 hours, from 7.5 hours to 10 hours, from 8 hours to 10 hours, from 3 hours to 9.5 hours, from 3 hours to 9 hours, from 3 hours to 8.5 hours, from 3 hours to 8 hours, from 3 hours to 7.5 hours, from 3 hours to 7 hours, from 3 hours to 6.5 hours, from 3 hours to 6 hours, from 3 hours to 5.5 hours, or even from 3 hours to 5 hours.

During the controlled transfer of the reaction mixture to quenching vessel 4, such as when the vacuum is applied to quenching vessel 4, a vapor stream from quenching vessel 4, which contains primarily $CO_2$, PO, and dibasic ester, may be vented to separation vessel 6 via conduit 24. In embodiments, conduit 24 may be connected to a bottom portion of the separation vessel 6. An exemplary separation vessel 6 may include a process scrubber, which in embodiments may be a distillation column. In embodiments, the $CO_2$ vapor stream from the top of the separation vessel 6 may be compressed and recycled back to $CO_2$ storage vessel 16 via conduit 7 or may be vented from the system via conduit 28. Additionally, in embodiments, dibasic ester may be added to the top of the separation vessel 6 via conduit 9. In embodiments, the purity of the recovered $CO_2$ may be at least 90%, at least 91%, at least 92%, at least 93%, at least 94%, at least 95%, at least 96%, at least 97%, at least 98%, or even at least 99%. In embodiments, the stream of $CO_2$ added to the polymerization reactor 2 through conduit 14 may comprise a mixture of fresh $CO_2$ and this recycled $CO_2$. The mixture may include, for instance, from 10 volume % (vol. %) to 30 vol. % recycled $CO_2$, such as from 15 vol. % to 25 vol. %, or even about 20 vol. %. In embodiments, the residue remaining in the quenching vessel 4 after vacuum stripping may be a mixture comprising the PPC polyol and dibasic ester, which may be collected via conduit 26 for further processing in processing unit 45.

In embodiments, the separation vessel 6 may be operated at different temperature ranges, such as one temperature range for the top of the separation vessel 6 and one temperature range for the bottom of the separation vessel 6. The top of the separation vessel 6 may be operated at a temperature from 20° C. to 25° C., from 20° C. to 24° C., from 20° C. to 23° C., from 20° C. to 22° C., from 20° C. to 21° C., from 21° C. to 25° C., from 21° C. to 23° C., from 22° C. to 25° C., from 23° C. to 25° C., or even from 24° C. to 25° C. Further, the top of the separation vessel 6 may be operated at a pressure from 10 kPaG to 15 kPaG, from 10 kPaG to 14 kPaG, from 10 kPaG to 13 kPaG, from 10 kPaG to 12 kPaG, from 10 kPaG to 11 kPaG, from 11 kPaG to 15 kPaG, from 12 kPaG to 15 kPaG, from 13 kPaG to 15 kPaG, or even from 14 kPaG to 15 kPaG. However, at the bottom of the separation vessel 6, the temperature may be from 30° C. to 45° C., from 30° C. to 44° C., from 30° C. to 43° C., from 30° C. to 42° C., from 30° C. to 41° C., from 30° C. to 40° C., from 30° C. to 39° C., from 30° C. to 38° C., from 30° C. to 37° C., from 30° C. to 36° C., from 30° C. to 35° C., from 31° C. to 45° C., from 32° C. to 45° C., from 33° C. to 45° C., from 34° C. to 45° C., from 35° C. to 45° C., from 35° C. to 41° C., from 36° C. to 45° C., from 37° C. to 45° C., from 38° C. to 45° C., from 39° C. to 45° C., or even from 40° C. to 45° C. Further, the bottom of the separation vessel 6 may be operated at a pressure from 20 kPaG to 40 kPaG, from 20 kPaG to 39 kPaG, from 20 kPaG to 38 kPaG, from 20 kPaG to 37 kPaG, from 20 kPaG to 36 kPaG, from 20 kPaG to 35 kPaG, from 20 kPaG to 34 kPaG, from 20 kPaG to 33 kPaG, from 20 kPaG to 32 kPaG, from 20 kPaG to 31 kPaG, from 20 kPaG to 30 kPaG, 21 kPaG to 40 kPaG, from 22 kPaG to 40 kPaG, from 23 kPaG to 40 kPaG, from 24 kPaG to 40 kPaG, from 25 kPaG to 40 kPaG, from 25 kPaG to 35 kPaG, from 26 kPaG to 40 kPaG, from 27 kPaG to 40 kPaG, from 28 kPaG to 40 kPaG, from 29 kPaG to 40 kPaG, or even from 30 kPaG to 40 kPaG.

The scrubbed PO in dibasic ester may first be passed to the collection vessel 30 through conduit 32 and then from the collection vessel 30 to the recovery vessel 8 through conduit 34. In embodiments, fresh dibasic ester solution from vessel 21 may be added near the top of the separation vessel 6 via conduit 9 to scrub the PO. The dibasic ester from collection vessel 30 may be cooled via heat exchanger 48 and then recirculated to the separation vessel 6 to scrub PO in the dibasic ester solution via conduit 33 for at least some batchwise embodiments. The recovery vessel 8 may separate certain impurities while separating the PO from the dibasic ester and, both of which may then be recycled for the production of PPC polyol. In embodiments, the recovery vessel 8 may comprise a distillation column with an associated reboiler 44, overhead receiver 6, and condenser 46. When a distillation column is used, the PO recycle stream may be produced as an overhead product, which may be sent to overhead receiver 36 via conduit 37 after cooling via condenser 46 and then sent from the overhead receiver 36 through conduit 40. In embodiments, the reflux stream from overhead receiver 36 may be returned back to the upper portion of recovery vessel 8 through conduit 38. In embodiments, a vent stream may be sent back to the bottom of separation vessel 6 through conduit 39 for further purification. In embodiments, the PO recycle stream may be sent to the PO storage vessel 12 to be reused in the formation of further PPC polyol via conduit 40. The PO recycle stream may pass through a molecular sieve dryer 43 to reduce the moisture content in the recycle stream. In embodiments, the resulting moisture content may be less than 50 ppm. The dibasic ester may be the bottoms product and may be collected through conduit 42. A vapor stream from reboiler 44 may be returned to the bottom of recovery vessel 8 through conduit 41. In embodiments, sufficiently pure dibasic ester may be recycled to the system, but in other embodiments, the dibasic ester may require further purification in the dibasic ester purification unit 47 before being of a satisfactory grade for use in the disclosed process.

In embodiments, the recovery vessel 8 may be operated at two different temperature ranges, one for the top of the recovery vessel 8 and one for the bottom of the recovery vessel 8. The top of the recovery vessel 8 may be operated at a temperature from 50° C. to 60° C., from 50° C. to 59° C., from 50° C. to 58° C., from 50° C. to 57° C., from 50° C. to 56° C., from 50° C. to 55° C., from 51° C. to 60° C., from 52° C. to 60° C., from 52° C. to 55° C., from 53° C. to 60° C., from 54° C. to 60° C., or even from 55° C. to 60° C. In embodiments, the top of the recovery vessel 8 may have a temperature of 54.1° C. Further, the top of the recovery vessel 8 may be operated at a pressure from 1 kPaG to 10 kPaG, from 1 kPaG to 9 kPaG, from 1 kPaG to 8 kPaG, from 1 kPaG to 7 kPaG, from 1 kPaG to 6 kPaG, from 1 kPaG to 5 kPaG, from 1 kPaG to 4 kPaG, from 1 kPaG to 3 kPaG, from 2 kPaG to 10 kPaG, from 3 kPaG to 10 kPaG, from 4 kPaG to 10 kPaG, from 5 kPaG to 10 kPaG, from 6 kPaG to 10 kPaG, from 7 kPaG to 10 kPaG, or even from 8 kPaG to 10 kPaG. In embodiments, the top of the recovery vessel 8 may be operated at a pressure of 6.89 kPaG. However, at the bottom of the recovery vessel 8, the temperature may be from 220° C. to 230° C., from 220° C.

to 229° C., from 220° C. to 228° C., from 220° C. to 227° C., from 220° C. to 226° C., from 220° C. to 225° C., from 221° C. to 230° C., from 222° C. to 230° C., from 223° C. to 230° C., from 224° C. to 230° C., from 224° C. to 228° C., or even from 225° C. to 230° C. In embodiments, the bottom of the recovery vessel 8 may have a temperature of 224.1° C. Further, the bottom of the recovery vessel 8 may be operated at a pressure from 1 kPaG to 10 kPaG, from 1 kPaG to 9 kPaG, from 1 kPaG to 8 kPaG, from 1 kPaG to 7 kPaG, from 1 kPaG to 6 kPaG, from 1 kPaG to 5 kPaG, from 1 kPaG to 4 kPaG, from 1 kPaG to 3 kPaG, from 2 kPaG to 10 kPaG, from 3 kPaG to 10 kPaG, from 4 kPaG to 10 kPaG, from 5 kPaG to 10 kPaG, from 6 kPaG to 10 kPaG, from 7 kPaG to 10 kPaG, or even from 8 kPaG to 10 kPaG. In embodiments, the bottom of the recovery vessel 8 may be operated at a pressure of 7.58 kPaG. In embodiments, the reflux ratio of the condensate returned to the column may be from 0.5 to 2.5, from 0.5 to 2.4, from 0.5 to 2.3, from 0.5 to 2.2, from 0.5 to 2.1, from 0.5 to 2, from 0.5 to 1.9, from 0.5 to 1.8, from 0.5 to 1.7, from 0.5 to 1.6, from 0.5 to 1.5, from 0.5 to 1.4, from 0.5 to 1.3, from 0.5 to 1.2, from 0.5 to 1.1, from 0.5 to 1, from 0.6 to 2.5, from 0.7 to 2.5, from 0.8 to 2.5, from 0.9 to 2.5, from 1 to 2.5, from 1.1 to 2.5, from 1.2 to 2.5, from 1.3 to 2.5, from 1.4 to 2.5, from 1.5 to 2.5, from 1.6 to 2.5, from 1.7 to 2.5, from 1.8 to 2.5, from 1.9 to 2.5, or even from 2 to 2.5. As used herein, the term "reflux ratio" refers to the ratio of reflux rate to distillate rate.

In one or more embodiments, a process for making PPC polyol may include using the PO collected in the process described above. For instance, an embodiment of the process for making PPC polyol may include introducing $CO_2$, PO, a starter, and at least one catalyst system to a reactor, thereby forming a mixture comprising the PPC polyol, unreacted PO, and $CO_2$. The reaction may take place in a batchwise fashion to make the desired PPC polyol under pressure. When the reaction is complete, the reactor batch may be transferred to the quenching vessel. Further, the process may include introducing the mixture comprising the PPC polyol, PO, and $CO_2$ to a quench system comprising the dibasic ester and an acid having a pKa from 0 to 16, and separating at least a portion of the PO and the $CO_2$ from the PPC polyol and the dibasic ester.

Referring again to the FIGURE, an apparatus 100 for the production of PPC polyol and isolation of excess $CO_2$, PO, and dibasic ester may include a polymerization reactor 2, a quenching vessel 4, a separation vessel 6, and a recovery vessel 8.

The polymerization reactor 2 may be fed reactants and catalysts through various conduits. For example, PO may be added to the polymerization reactor 2 through conduit 10 from PO storage vessel 12. In addition, $CO_2$ may be added to the polymerization reactor 2 through conduit 14 from $CO_2$ storage vessel 16. Finally, other raw materials, such as the catalyst and the starter, may be added to the polymerization reactor 2 through one or more conduits 18 from one or more storage vessels 20. The flow rate through the one or more conduits 10, 14, 18 may vary based on the nature of material added for conduits 18, as well as the product grade, and pressurization of the system for conduits 10, 14, 18.

The temperature of the polymerization reactor 2 may be maintained from 25° C. to 100° C., such as from 30° C. to 95° C., from 30° C. to 90° C., from 30° C. to 85° C., from 30° C. to 80° C., from 30° C. to 75° C., from 30° C. to 70° C., from 30° C. to 65° C., from 30° C. to 60° C., from 30° C. to 55° C., from 30° C. to 50° C., from 30° C. to 45° C., from 30° C. to 40° C., from 30° C. to 35° C., from 35° C. to 100° C., from 40° C. to 100° C., from 45° C. to 100° C., from 50° C. to 100° C., from 55° C. to 100° C., from 60° C. to 100° C., from 65° C. to 100° C., from 70° C. to 100° C., from 75° C. to 100° C., from 80° C. to 100° C., from 85° C. to 100° C., from 90° C. to 100° C., or even from 95° C. to 100° C. Further, during the polymerization reaction, the polymerization reactor 2 may be under $CO_2$ pressure from 1 MPa to 10 MPa, from 1 MPa to 9 MPa, from 1 MPa to 8 MPa, from 1 MPa to 7 MPa, from 1 MPa to 6 MPa, from 1 MPa to 5 MPa, from 1 MPa to 4 MPa, from 1 MPa to 3 MPa, from 2 MPa to 10 MPa, from 3 MPa to 10 MPa, from 4 MPa to 10 MPa, from 5 MPa to 10 MPa, from 6 MPa to 10 MPa, from 7 MPa to 10 MPa, or even from 8 MPa to 10 MPa.

In embodiments, at least one catalyst may include catalysts described in U.S. Pat. No. 8,633,123, the entire content of which is incorporated herein by reference. For instance, the catalyst may include metal complexes having an activating species tethered to a multidentate ligand that is coordinated to an active metal center of the metal complex.

In embodiments, the starter may comprise one or more heavy glycols. As used herein, the term "heavy glycols" refers to glycols having a molecular weight from 100 Daltons to 25,000 Daltons, from 100 Daltons to 20,000 Daltons, from 100 Daltons to 15,000 Daltons, from 100 Daltons to 10,000 Daltons, from 100 Daltons to 5,000 Daltons, from 100 Daltons to 1,000 Daltons, from 100 Daltons to 500 Daltons, from 500 Daltons to 25,000 Daltons, from 1,000 Daltons to 25,000 Daltons, from 5,000 Daltons to 25,000 Daltons, from 10,000 Daltons to 25,000 Daltons, from 15,000 Daltons to 25,000 Daltons, or even from 20,000 Daltons to 25,000 Daltons. Exemplary heavy glycols include, but are not limited to, dipropylene glycol (DPG) and triethylene glycol (TEG).

According to a first aspect, either alone or in combination with any other aspect, a process includes introducing a mixture comprising polypropylene carbonate (PPC) polyol, carbon dioxide, propylene oxide, and at least one dibasic ester to a quenching vessel to separate the PPC polyol from the carbon dioxide and the propylene oxide; introducing additional dibasic ester to the separation vessel, thereby separating the carbon dioxide from the propylene oxide and the dibasic ester such that a mixture of propylene oxide and the dibasic ester is formed; and introducing the mixture of propylene oxide and the dibasic ester to a recovery vessel, wherein the propylene oxide is separated from the dibasic ester in the recovery vessel.

According to a second aspect, either alone or in combination with any other aspect, the at least one dibasic ester is selected from the group consisting of di-methyl adipate, di-methyl glutarate, di-methyl succinate, di-ethyl adipate, diethyl glutarate, di-ethyl succinate, and a combination of two or more thereof.

According to a third aspect, either alone or in combination with any other aspect, the at least one dibasic ester comprises dimethyl succinate.

According to a fourth aspect, either alone or in combination with any other aspect, the at least one dibasic ester is dimethyl succinate.

According to a fifth aspect, either alone or in combination with any other aspect, the recovery vessel comprises a distillation column.

According to a sixth aspect, either alone or in combination with any other aspect, the recovery vessel comprises at least one distillation column from which the propylene oxide evolves as an overhead product and the dibasic ester evolves as a bottoms product.

According to a seventh aspect, either alone or in combination with any other aspect, a source of the mixture comprising carbon dioxide, propylene oxide, and at least one dibasic ester is a reactor.

According to an eighth aspect, either alone or in combination with any other aspect, the carbon dioxide from the separation vessel is recycled to the reactor.

According to a ninth aspect, either alone or in combination with any other aspect, the carbon dioxide from the separation vessel is vented.

According to a tenth aspect, either alone or in combination with any other aspect, the at least one dibasic ester from the recovery vessel is recycled to the reactor.

According to a eleventh aspect, either alone or in combination with any other aspect, the recovery vessel has a top portion and a bottom portion, the top portion operated at a temperature from 50° C. to 60° C. and a pressure from 1 kPaG to 10 kPaG and the bottom portion operated at a temperature from 220° C. to 230° C. and a pressure from 1 kPaG to 10 kPaG.

According to a twelfth aspect, either alone or in combination with any other aspect, the recovery vessel has a top portion and a bottom portion, the top portion operated at a temperature from 50° C. to 55° C. and a pressure from 1 kPaG to 10 kPaG and the bottom portion operated at a temperature from 224° C. to 228° C. and a pressure from 1 kPaG to 10 kPaG.

Examples

Using embodiments described above, an exemplary scheme for producing PPC polyol was conducted as follows. The following examples are merely illustrative and should not be interpreted as limiting the scope of the present disclosure.

Introduction

Experimental Vapor-liquid equilibrium measurements were obtained for PO-DBE(4), PO—$CO_2$, and DBE(4)-$CO_2$ binary systems at different isotherms to understand the vapor liquid phase behavior. The experimental vapor liquid equilibrium data were regressed and modeled with a best fit thermodynamic model using Aspen Plus V10. Then, x-y diagrams (x and y represent liquid and vapor phase molar composition) and Pxy (pressure vs composition) diagrams were developed to understand the vapor liquid phase behavior and recovery process design.

Validation of a PPC polyol production process in accordance with embodiments disclosed herein was conducted in five phases. In Phase I, PPC polyol production was performed at the 2-liter lab scale. In Phase II, PPC polyol production was performed at a 25-liter (6.6 gallon) scale. In Phase III, PPC polyol production was performed at a 250-liter (66 gallon) pilot scale with PO recovery. In Phase IV, PPC polyol production was performed at a 250-liter (66 gallon) pilot scale using PO recovered in Phase III. In Phase V, two runs of the PPC polyol production with fresh PO and two runs of the PPC polyol production using PO recovered from Phase IV were performed, both at a 250-liter (66 gallon) pilot scale.

Phase I and Phase II were conducted to validate the process and the analytical techniques employed.

In Phase III, a baseline polymerization run was conducted using a 250-liter pilot scale reactor. Unreacted PO was captured using a di-methyl succinate-based scrubber and recovered using a distillation column. This "first recovered PO" was analyzed for impurities using GC/MS.

In phase IV, one polymerization run was conducted using 75% fresh PO and 25% recovered PO (by mass) from the first recovered PO of Phase III. Unreacted PO was captured using a di-methyl succinate-based scrubber and recovered using a distillation column. This "second recovered PO" was analyzed for impurities using GC/MS.

In Phase V, an additional baseline reaction using 100% fresh PO and two additional polymerization runs using a mixture of fresh PO and the second recovered PO of Phase IV were conducted. One of the runs using a mixture of fresh and second recovered PO was conducted using 75% fresh PO and 25% recovered PO by mass, and another of the runs was conducted using 85% fresh PO and 15% recovered PO by mass. Unreacted PO was captured using a di-methyl succinate-based scrubber and recovered using a distillation column. This "third recovered PO" was analyzed for impurities using GC/MS.

General Process Flow

A general process description for Phases III-V is as follows. The reactor is pre-cleaned and conditioned. Once pre-cleaning and conditioning of the reactor was complete, starter (dipropylene glycol) was added to the reactor and dried via nitrogen sparge. Solid catalyst and co-catalyst were then added to the reactor. The reactor was charged with PO and vaporized $CO_2$ from supply tanks. Although the reaction is exothermic, operating temperatures are moderate and were controlled between 30° C. and 35° C. The reaction was run under moderate $CO_2$ pressure (approximately 1.4 MPa or 200 psi) and mixed via an agitator or external recirculation loop. As the reaction progressed, $CO_2$ pressure was maintained at 1.4 MPa (200 psi) until the reaction was deemed complete.

At the end of the polymerization, the reactor contents were transferred to the quenching vessel with controlled venting to a process scrubber, to bring the pressure down to near atmospheric. The reaction was quenched using a strong acid, such as hypophosphorous acid, in di-methyl succinate, resulting in an approximately 50 wt. % solution of PPC polyol in di-methyl succinate. A vapor stream, comprising primarily $CO_2$ and PO, was vented through a process scrubber while recirculating di-methyl succinate at a constant flow rate from a solvent tank through the process scrubber.

Following the atmospheric venting of the gas, the bulk of the PO remaining in the quench tank was removed under vacuum at 45° C. Finally, the PPC polyol solution temperature was increased to 70° C. to reduce color and to remove the remaining PO. The di-methyl succinate, which was recirculated counter-currently through the scrubber, absorbed the PO from the passing vapor flow during atmospheric venting and the vacuum stripping process. The resulting PO-rich di-methyl succinate was collected in a solvent tank. When the unreacted PO removal was complete, PPC polyol product with di-methyl succinate was transferred to a downstream recovery system.

Table 1 summarizes the material input at each stage of the process described and the material output from the polymerization reactor.

TABLE 1

Material input and output of an exemplary pilot-scale reaction

| System | Material | Amount (kg) |
| --- | --- | --- |
| Polymerization Reactor Inputs | Poly-G 20-112 | 60.8 |
|  | PO | 52 |
|  | Catalyst | 0.072 |

TABLE 1-continued

Material input and output of an exemplary pilot-scale reaction

| System | Material | Amount (kg) |
|---|---|---|
| Polymerization Reactor Outputs | $CO_2$ | 40 |
| | Co-catalyst | 0.0072 |
| | PPC polyol | 129.3 |
| | PO | 13 |
| Quench | $CO_2$ | 6 |
| | Catalyst | Trace[1] |
| | 50% $H_3PO_2$ | 0.119 |
| | Di-methyl succinate | 106 |

[1] As used herein, the term "trace" refers to a negligible amount, such as from 1 gram to 5 grams Impurities To compare the impurities found in recycled PO to those found in fresh PO, GC/MS was performed on a fresh sample of PO, that is, the PO fed into Phase III, and the first recovered PO, second recovered PO, and third recovered PO. Additionally, the third recovered PO was subjected to a molecular sieve treatment, and the resulting PO was also analyzed by GC/MS. The impurities levels in the first and third recovered PO and the molecular sieve treated sample from third recovered PO were all within 0.2% of the fresh PO, with individual impurities levels less than 0.015%.

The sample from the first recovered PO had impurities that were not present in either fresh PO or in the other recovered PO samples. This was the first distillation run through the process apparatus and would have "cleaned" the equipment ahead of obtaining the second recovered PO. Therefore, the sample appears contaminated and is not representative of the recycle process. Further, the sample from the third recovered PO had abnormal impurities, including di-methyl succinate (0.14%), methanol (0.13%), water (0.1%), and acetaldehyde (0.008%), none of which are believed to interfere with the reaction kinetics or product quality.

Without intending to be bound by any particular theory, it is believed that the reasons for these impurities are three-fold. First, regarding the water and methanol, the run leading to the third recovered PO was more efficient, with 96% of the theoretical PO recovered, compared to the run leading to the first recovered PO, with 56% of the theoretical PO recovered, and the second recovered PO, with 69% of the theoretical PO recovered. This increased PO recovery may have carried higher amounts of water to the PO recovery column, where the water was accumulating from the previous recovery runs, leading to di-methyl succinate hydrolysis products, such as methanol. Second, regarding acetaldehyde, vendors' certificates of analysis of commercial PO typically include levels of acetaldehydes (or sometimes total aldehydes). Each successive polymerization would enhance this impurity if it was not consumed or removed in the polymerization and PO capture. Third, it is noted that the temperature in the recovery column bottom in one of the runs was 4° C. to 5° C. hotter than that of earlier runs, perhaps leading to higher impurity levels (di-methyl succinate, methanol, and water) in the recovered PO.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that that the mere use of the term "first" and "second" does not require that there be any "third" component, although that possibility is contemplated under the scope of the present disclosure.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

What is claimed is:

1. A process comprising:
   introducing a mixture comprising polypropylene carbonate (PPC) polyol, carbon dioxide, propylene oxide, and at least one dibasic ester to a quenching vessel to separate the PPC polyol from the carbon dioxide and the propylene oxide;
   introducing additional dibasic ester to the separation vessel, thereby separating the carbon dioxide from the propylene oxide and the dibasic ester such that a mixture of propylene oxide and the dibasic ester is formed; and
   introducing the mixture of propylene oxide and the dibasic ester to a recovery vessel, wherein the propylene oxide is separated from the dibasic ester in the recovery vessel.

2. The process of claim 1, wherein the at least one dibasic ester is selected from the group consisting of di-methyl adipate, di-methyl glutarate, di-methyl succinate, di-ethyl adipate, diethyl glutarate, di-ethyl succinate, and a combination of two or more thereof.

3. The process of claim 1, wherein the at least one dibasic ester comprises dimethyl succinate.

4. The process of claim 1, wherein the at least one dibasic ester is dimethyl succinate.

5. The process of claim 1, wherein the recovery vessel comprises a distillation column.

6. The process of claim 1, wherein the recovery vessel comprises at least one distillation column from which the propylene oxide evolves as an overhead product and the dibasic ester evolves as a bottoms product.

7. The process of claim 1, wherein a source of the mixture comprising carbon dioxide, propylene oxide, and at least one dibasic ester is a reactor.

8. The process of claim 7, wherein the carbon dioxide from the separation vessel is recycled to the reactor.

9. The process of claim 1, wherein the carbon dioxide from the separation vessel is vented.

10. The process of claim 7, wherein the at least one dibasic ester from the recovery vessel is recycled to the reactor.

11. The process of claim 1, wherein the recovery vessel has a top portion and a bottom portion, the top portion operated at a temperature from 50° C. to 60° C. and a pressure from 1 kPaG to 10 kPaG and the bottom portion operated at a temperature from 220° C. to 230° C. and a pressure from 1 kPaG to 10 kPaG.

12. The process of claim 1, wherein the recovery vessel has a top portion and a bottom portion, the top portion operated at a temperature from 50° C. to 55° C. and a pressure from 1 kPaG to 10 kPaG and the bottom portion operated at a temperature from 224° C. to 228° C. and a pressure from 1 kPaG to 10 kPaG.

\* \* \* \* \*